(12) United States Patent
Spaller et al.

(10) Patent No.: US 9,403,876 B2
(45) Date of Patent: *Aug. 2, 2016

(54) CYCLIC-GLUR6 ANALOGS, METHODS OF TREATMENT AND USE

(75) Inventors: Mark Spaller, Lebanon, NH (US); John Marshall, Providence, RI (US); Dennis J. Goebel, Detroit, MI (US)

(73) Assignee: Brown University, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/320,848

(22) PCT Filed: May 18, 2010

(86) PCT No.: PCT/US2010/035188
§ 371 (c)(1),
(2), (4) Date: May 22, 2012

(87) PCT Pub. No.: WO2010/135277
PCT Pub. Date: Nov. 25, 2010

(65) Prior Publication Data
US 2012/0220535 A1   Aug. 30, 2012

Related U.S. Application Data

(60) Provisional application No. 61/179,055, filed on May 18, 2009.

(51) Int. Cl.
| A61K 38/12 | (2006.01) |
| C07K 5/00  | (2006.01) |
| C07K 7/00  | (2006.01) |
| C07K 16/00 | (2006.01) |
| C07K 17/00 | (2006.01) |
| C07K 7/56  | (2006.01) |
| A61K 38/00 | (2006.01) |

(52) U.S. Cl.
CPC . *C07K 7/56* (2013.01); *A61K 38/00* (2013.01); *Y10T 428/2982* (2015.01)

(58) Field of Classification Search
CPC .............. C07K 14/705; C07K 2319/00; C07K 14/4702; A61K 38/00
See application file for complete search history.

(56) References Cited

U.S. PATENT DOCUMENTS

| 4,033,940 A | 7/1977 | Hughes et al. |
| 4,102,877 A | 7/1978 | Nutt |
| 7,141,600 B2 | 11/2006 | Guy et al. |
| 7,510,824 B2 | 3/2009 | Tymianski |
| 8,673,857 B2 * | 3/2014 | Marshall et al. ............ 514/17.8 |
| 2003/0219378 A1 * | 11/2003 | Piwnica-Worms .......... 424/1.69 |
| 2005/0281816 A1 * | 12/2005 | Lamping et al. ............ 424/144.1 |
| 2006/0029544 A1 | 2/2006 | Sutcliffe-Goulden et al. |
| 2007/0207502 A1 | 9/2007 | Benkovic et al. |
| 2009/0105116 A1 | 4/2009 | Ni et al. |

OTHER PUBLICATIONS

Piserchio et al., 2004, Chemistry & Biology, vol. 11, 469-473.*
Piserchio et al., "Targeting Specific PDZ Domains of PSD-95: Structural Basis for Enhanced Affinity and Enzymatic Stability of a Cyclic Peptide", Chemistry & Biology 2004, 11:469-473.
Rothbard et al., "Conjugation of arginine oligomers to cyclosporin a facilitates topical delivery and inhibition of inflammation", Nature Medicine 2000, 6(11):1253-1257; p. 1255 Fig. 4.
Tao et al., "Thermodynamic profiling of conformationally constrained cyclic ligands for the PDZ domain", Bioorganic & Medicinal Chemistry Letters 2004, 14:1385-1388, p. 1387 Fig. 3.
Udugamasooriya et al. "Bridged Peptide Macrocycles as Ligands for PDZ Domain Proteins", Organic Letters 2005, 7(7):1203-1206.
Sharma et al., "Design, Synthesis, and Evaluation of Linear and Cyclic Peptide Ligands for PDZ10 of the Multi-PDZ Domain Protein MUPP1", Biochemistry 2007, 46:12709-12720.
Joo, "Synthesis and screening of support-bound combinatorial cyclic peptides and free C-terminal peptide libraries", The Ohio State Univeristy 2007, [Retrieved 3 from the Internet on Aug. 2010 at http://etd.ohiolink.edu/send-pdf.cgi/Joo%20Sang%20Hoon.pdf?osu1195561420].

(Continued)

*Primary Examiner* — James H Alstrum Acevedo
*Assistant Examiner* — Kaipeen Yang
(74) *Attorney, Agent, or Firm* — Thomas M. Saunders

(57) ABSTRACT

A composition which is reversible inhibitor of at least one neuron-specific PDZ domain comprising

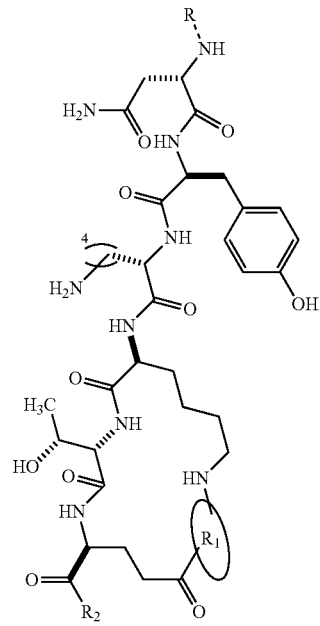

Structure 5 wherein
R is a molecular transporter with or without a linker amino acid;
$R_1$ is at least about one amino acid covalently bound; and,
$R_2$ is isoleucine, leucine, alanine, phenylalanine, or valine, and methods of use.

22 Claims, 1 Drawing Sheet

(56) References Cited

OTHER PUBLICATIONS

LeBlanc et al., "A cyclic peptide targeted against PSD-95 blocks centrla sensitizaiton and attenuates thermal hyperalhesia", Neuroscience Epub Feb. 20110, 167(2):490-500, p. 491 Fig. 1.
PCT/US2010/035188 International Search Report dated Jan. 20, 2011.
Blazer et al., "Small Molecule Protein-Protein Interaction Inhibitors as CNS Theraputic Agents: Current Progress and Future Hurdles," (Neuropsychopharmacology, 1-16, (2008)).
Rupasinghe et al., "The interplay between structure-based design and combinatorial chemistry," Current Opinion in Chemical Biology, 10, 188-193 (2006).
Cui et al. "PDZ protein interactions underlying NMDA receptor mediated excitotoxicity and neuroprotection by PSD-95 inhibitors," J. Neuroscience, 27, 9901-9915 (2007).
Klosi et al., "Bivalent peptides as PDZ domain ligands," Bioorganic & Medicinal Chemistry Letters, 17, 6147-6150 (2007).
Saro et al. "A thermodynamic ligand binding study of the third PDZ domain (PDZ3) from the Mammalian Neuronal Protein PSD-95," NIH, 46, 6340-6352, (2008).
Udugamasooriya et al. "A chemical library approach to organic-modified peptide ligands for PDZ domain proteins: A synthetic, thermodynamic and structural investigation," Chem. Bio. Chem., 9, 1587-1589 (2008).
Udugamasooriya et al. "Conformational constraint in protein ligand design and the inconsistency of binding entropy." Biopolymers, 89, 653-667 (2008).
Tao Li, "Studies of ligand-protein interaction for the third PDZ domain (PDZ3) of mammalian post-synaptic density-95 (PSD-95)" (Jan. 1, 2005). ETD Collection for Wayne State University. Paper AAI3198697. http://digitalcommons.wayne.edu/dissertations/AAI3198697.
Goun et al. "Molecular Transporters: Synthesis of Oligoguanidinium Transporters and Their Application to Drug Delivery and Real-Time Imaging," ChemBioChem, 7:1479-1515 (2006).
Stewart et al., "Cell-penetrating peptides as deliver vehicles for biology and medicine," Org. Biomol. Chem., 6:2242-2255 (2008).
Camerero, J. A., and Muir, T. W., J. Am. Chem. Society. 121:5597 (1999).
Wu, H. et al, Proc. Natl. Acad. Sci. USA, 95:9226 (1998).
Martin Linhult et al., "Evaluation of different linker regions for multimerization and coupling chemistry for immobilization of a proteinaceous affinity ligand," Protein Engineering, vol. 16 No. 12 pp. 1147-1152, Oxford University Press (2003).

* cited by examiner

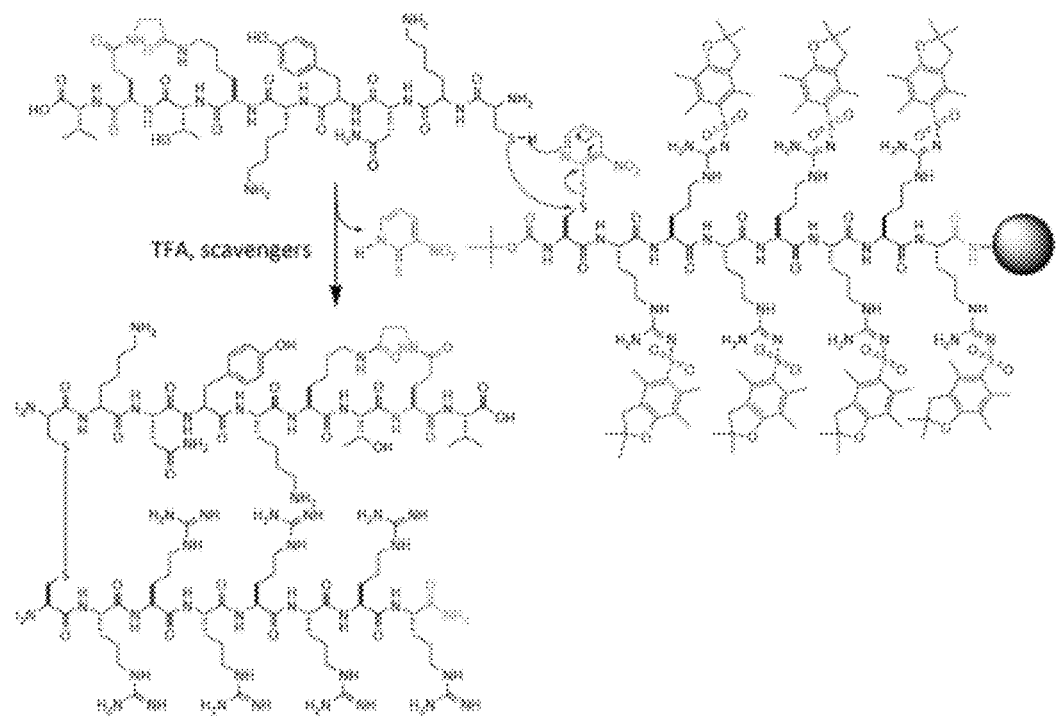

SEQUENCE LISTING

<160> NUMBER OF SEQ ID NOS: 15

<210> SEQ ID NO 1
<211> LENGTH: 4
<212> TYPE: PRT
<213> ORGANISM: Unknown
<220> FEATURE:
<223> OTHER INFORMATION: Description of Unknown: PDZ domain peptide

<400> SEQUENCE: 1

Gly Leu Gly Phe
1

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: Sequence may be 6-20 residues in length

<400> SEQUENCE: 2

Arg Arg Arg Arg Arg Arg Arg Arg Arg Arg Arg Arg Arg Arg Arg
1               5                   10                  15

Arg Arg Arg Arg
            20

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Arg Arg Arg Arg Arg Arg
1               5

<210> SEQ ID NO 4
<211> LENGTH: 9
<212> TYPE: PRT
<213> ORGANISM: Human immunodeficiency virus 1

<400> SEQUENCE: 4

Arg Lys Lys Arg Arg Gln Arg Arg Arg
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Arg Arg Arg Arg Arg Arg Arg Arg
1               5

<210> SEQ ID NO 6
<211> LENGTH: 16
<212> TYPE: PRT

```
<213> ORGANISM: Unknown
<220> FEATURE:
<223> OTHER INFORMATION: Description of Unknown: Penetratin
      (Antennapedia) peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 21
<212> TYPE: PRT
<213> ORGANISM: Unknown
<220> FEATURE:
<223> OTHER INFORMATION: Description of Unknown: Pep-1 peptide

<400> SEQUENCE: 7

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 8
<211> LENGTH: 27
<212> TYPE: PRT
<213> ORGANISM: Unknown
<220> FEATURE:
<223> OTHER INFORMATION: Description of Unknown: Transportan peptide

<400> SEQUENCE: 8

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 9
<211> LENGTH: 10
<212> TYPE: PRT
<213> ORGANISM: Unknown
<220> FEATURE:
<223> OTHER INFORMATION: Description of Unknown: Nuclear localization
      peptide

<400> SEQUENCE: 9

Val Gln Arg Lys Arg Gln Lys Leu Met Pro
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Description of Unknown: Nuclear localization
      peptide

<400> SEQUENCE: 10

Ser Lys Lys Lys Lys Ile Lys Val
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Unknown: Nuclear localization
      peptide
```

```
<400> SEQUENCE: 11

Gly Arg Lys Arg Lys Lys Arg Thr
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Thr Glu Val
1

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys(Npys)

<400> SEQUENCE: 13

Cys Arg Arg Arg Arg Arg Arg Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(7)
<223> OTHER INFORMATION: Arg(Pbf)

<400> SEQUENCE: 14

Arg Arg Arg Arg Arg Arg Arg
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys(Npys)
<220> FEATURE:
<221> NAME/KEY: MOD_RES
<222> LOCATION: (2)..(8)
<223> OTHER INFORMATION: Arg(Pbf)

<400> SEQUENCE: 15

Cys Arg Arg Arg Arg Arg Arg Arg
1               5
```

CYCLIC-GLUR6 ANALOGS, METHODS OF TREATMENT AND USE

CROSS REFERENCE TO RELATED APPLICATIONS

This application is a national phase application of, and claims priority to, PCT/US2010/035188, filed on May 18, 2010, which claims the benefit of priority under 35 U.S.C. §119(e) to U.S. Patent Application No. 61/179,055 filed on May 18, 2009, the disclosures of which are incorporated herein in their entirety by reference.

STATEMENT OF GOVERNMENT RIGHTS

This invention was made with government support under R01 DA018428 and R21 NS061176 awarded by National Institutes of Health. The government has certain rights in the invention.

SEQUENCE LISTING

The instant application contains a Sequence Listing which has been submitted via EFS-Web and is hereby incorporated by reference in its entirety. Said ASCII copy, created on Jun. 17, 2010, is named B0197006.txt and is 4,120 bytes in size.

FIELD OF THE INVENTION

A composition which is reversible inhibitor of at least one neuron-specific PDZ domain comprising

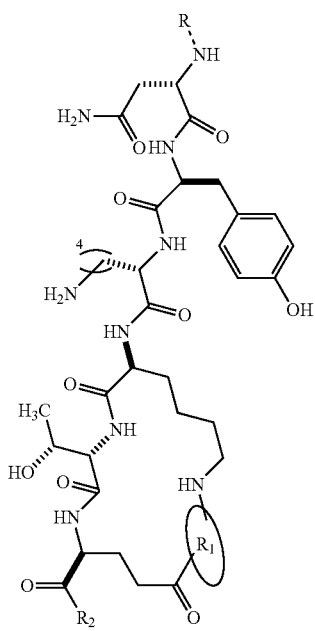

Structure 5 wherein

R is a molecular transporter with or without a linker amino acid;

$R_1$ is at least about one amino acid covalently bound; and, $R_2$ is isoleucine, leucine, alanine, phenylalanine, or valine, and methods of use.

BACKGROUND OF THE INVENTION

The PDZ domain is a common structural domain of 80-90 amino-acids found in the signaling proteins of bacteria, yeast, plants, and animals. PDZ is an acronym combining the first letters of three proteins—post synaptic density protein (PSD95), Drosophila disc large tumor suppressor (DlgA), and zonula occludens-1 protein (zo-1)—which were first discovered to share the domain. PDZ domains are also referred to as DHR (Dlg homologous region) or GLGF (glycine-leucine-glycine-phenylalanine) (SEQ ID NO: 1) domains. These domains have been reported as helping to anchor transmembrane proteins to the cytoskeleton and hold together signaling complexes.

There are roughly 260 human PDZ domains, though since several PDZ domain containing proteins hold several domains, the actual number of PDZ proteins is closer to 180. Blazer et al., "Small Molecule Protein-Protein Interaction Inhibitors as CNS Theraputic Agents: Current Progress and Future Hurdles," (*Neuropsychopharmacology*, 1-16, (2008)) (the teachings of which are incorporated herein by reference) states that "PDZ domains are important scaffolding components in many signaling systems, with an extensive role in the development and maintenance of both pre- and post-synaptic structures. Development of reversible small molecule inhibitors that target neuron-specific PDZ domains would provide useful tools to probe the many functions of these important scaffolds." In a drug discovery program, stable, selective, high affinity chemical probes for PDZ domains will be useful in the identification and quantification of cellular protein therapeutic candidates having endogenous activity at the PDZ binding modules. Attention is drawn to Udugamasooriya et al., "*Bridged Peptide Macrocycles as Ligands for PDZ Domain Proteins,*" *Organic Letters,* 7(7):1203-1206 (2005), the teachings of which are incorporated herein by reference.

It has been reported that glutamate is the most prominent neurotransmitter in human physiology as present in over 50% of nervous tissue. Without being bound by any particular theory, it is believed that glutamate acts upon two classes of receptors, one containing a ligand-gated cation pore, called ionotropic glutamate receptors and the other class that responds to glutamate by mediating second-messenger proteins, called metabotropic glutamate receptors. The ionotropic receptors are further classified based upon preferential agonist binding/activation by N-methyl-D-aspartate (NMDA-receptors), AMPA-receptors and kainate-receptors. All three glutamate receptors are permeable to sodium with the NMDA-R having a preference for calcium, and, when activated by glutamate, these ions enter the neuron through the central pore of the receptor, leading the neuron to depolarize.

Also noted are the following, the teachings of which are incorporated herein by reference (as are all references cited in this document):

1. Li et al., "Thermodynamic profiling of conformationally constrained cyclic ligands for the PDZ domain,"*Bioorganic & Medicinal Chemistry Letters*, 14, 1385-1388 (2004)
2. Guy et al. "Small molecule inhibition of PDZ-Domain interaction," U.S. Pat. No. 7,141,600.
3. Chamila N. Rupasinghe and Mark R. Spaller, "The interplay between structure-based design and combinatorial chemistry," *Current Opinion in Chemical Biology*, 10, 188-193 (2006).
4. Sharma et al., "Design, synthesis, and evaluation of linear and cyclic peptide ligands for PDZ10 of the multi-PDZ domain protein MUPP1," *Biochemistry*, 46, 12709-12720 (2007).
5. Cui et al. "PDZ protein interactions underlying NMDA receptor mediated excitotoxicity and neuroprotection by PSD-95 inhibitors," *J. Neuroscience*, 27, 9901-9915 (2007).
6. Klosi et al., "Bivalent peptides as PDZ domain ligands," *Bioorganic & Medicinal Chemistry Letters*, 17, 6147-6150 (2007).
7. Saro et al. "A thermodynamic ligand binding study of the third PDZ domain (PDZ3) from the Mammalian Neuronal Protein PSD-95," *NIH*, 46, 6340-6352. (2008).
8. Gomika et al. "A chemical library approach to organic-modified peptide ligands for PDZ domain proteins: A synthetic, thermodynamic and structural investigation," *Chem. Bio. Chem.*, 9, 1587-1589 (2008).
9. D. Gomika Udugamasooriya and Mark R. Spaller "Conformational constraint in protein ligand design and the inconsistency of binding entropy." *Biopolymers*, 89, 653-667 (2008).
10. Tao Li, "Studies of ligand-protein interaction for the third PDZ domain (PDZ3) of mammalian post-synaptic density-95 (PSD-95)" (Jan. 1, 2005). *ETD Collection for Wayne State University*. Paper AAI3198697. http://digitalcommons.wayne.edu/dissertations/AAI3198697
11. Sutcliffe-Goulden et al., "Receptor-binding cyclic peptides and methods of use," U.S. Ser. No. 11/198,884 (2005).

Further mention is made of Goun et al. "Molecular Transporters: Synthesis of Oligoguanidinium Transporters and Their Application to Drug Delivery and Real-Time Imaging," *ChemBioChem*, 7:1479-1515 (2006) and Stewart et al., "Cell-penetrating peptides as deliver vehicles for biology and medicine," *Org. Biomol. Chem.*, 6:2242-2255 (2008), *The Handbook of Cell-Penetrating Peptides, Second Edition*, Ülo Langel, Ed, CRC (2006), and *Cell-Penetrating Peptides Processes and Applications*, Ülo Langel, Ed, CRC (2002).

Various methods for producing cyclic peptides have been described. For example, chemical reaction protocols, such as those described in U.S. Pat. Nos. 4,033,940 and 4,102,877, have been devised to produce circularized peptides. In other techniques, biological and chemical methods are combined to produce cyclic peptides. Some methods involve first expressing linear precursors of cyclic peptides in cells (e.g., bacteria) to produce linear precursors of cyclic peptides and then adding of an exogenous agent such as a protease or a nucleophilic reagent to chemically convert these linear precursors into cyclic peptides. See, e.g., Camerero, J. A., and Muir, T. W., J. Am. Chem. Society. 121:5597 (1999); Wu, H. et al, Proc. Natl. Acad. Sci. USA, 95:9226 (1998).

Also noted are Martin Linhult et al., "Evaluation of different linker regions for multimerization and coupling chemistry for immobilization of a proteinaceous affinity ligand," *Protein Engineering*, vol. 16 no. 12 pp. 1147-1152, Oxford University Press (2003).

BRIEF DESCRIPTION OF THE DRAWINGS

FIG. 1 is a diagram of the reaction between on-resin 3-nitro-2-pyridinesulphenyl (Npys) protected cysteine-ologoarginine and unprotected cysteine containing macrocyclic ligand.

SUMMARY OF THE INVENTION

This invention comprises a composition which is reversible inhibitor of at least one neuron-specific PDZ domain comprising

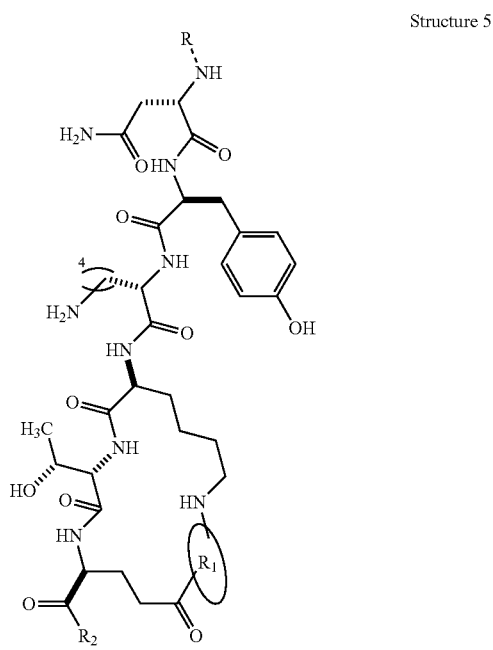

Structure 5 wherein
R is a molecular transporter with or without a linker amino acid;
$R_1$ is at least about one amino acid covalently bound; and,
$R_2$ is isoleucine, leucine, alanine, phenylalanine, or valine.
In some embodiments, $R_1$ is β-alanine. In particular embodiments, $R_2$ is valine. It is contemplated that in some embodiments the $P_{-4}$ position is lysine, aspartic acid, glutamic acid or arginine. In a specific embodiment, the composition has the structure:

Structure 1

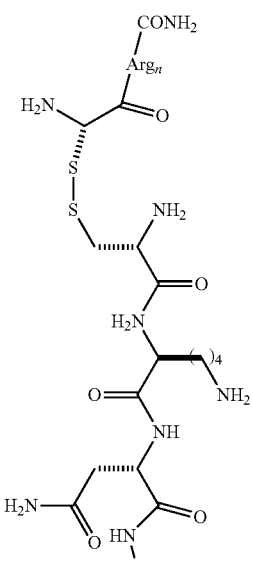

or:

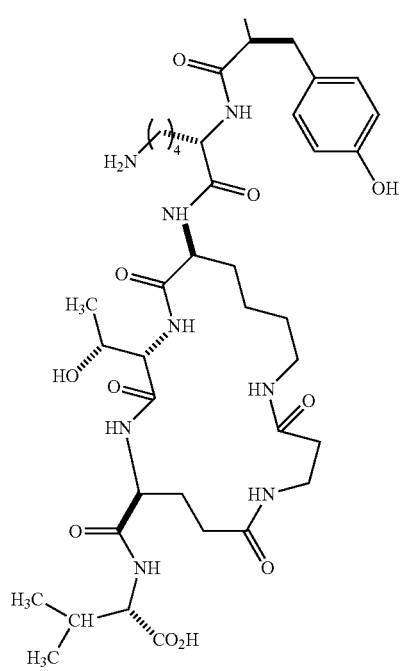

Structure 2

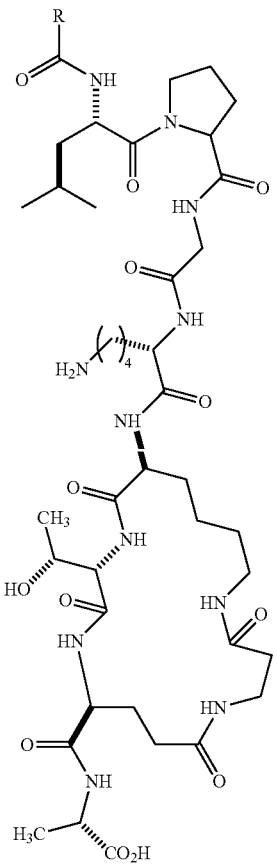

In some embodiments R comprises a liposome, steroid, polyamine, nanotube, nanoparticle, dendrimer, cell-penetrating peptide, protein-transduction domain amino acid, peptoid, (N-substituted glycine), oligogcarbamate, arginine oligomer of about 6-20 units (SEQ ID NO: 2) D-arginine oligomer, spaced arginine oligomer, N-arginine peptoid, oligoarbamate transporter, or tetrameric dendrimer. In addition R may comprise (SEQ ID NO: 3)

Structure 3:

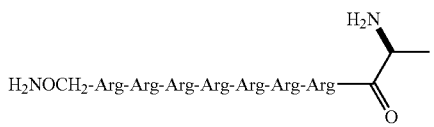

Poly Arg Tail

The practice of this invention further contemplates a method of treatment of neuro-stress comprising administering to a subject a therapeutically effective amount of the composition of Structure 5. In specific embodiments of the method of neuro-stress is selected from the group comprising stroke, traumatic brain injury, epilepsy, pain or neurodegenerative disease. It is particularly contemplated that the method employs administration in advance of said neuro-stress and is also contemplated for therapeutic intervention against further neuronal damage from the neuro-stress. Further contemplated is cotreatment with a therapeutically effective amount of an NMDA receptor antagonists such as memantine, ketamine, select NMDA-R2B antagonists or current neuro-protective therapeutics such as mannitol. Cotreating agents are administered before, after or at generally the same time as the compositions of Structure 5.

The method of treatment encompasses therapeutic effective dose of the composition of Structure 5 from about 0.1 μM to about 100 μM, and particularly from about 20 μM to about 40 μM. Administration includes parenteral, oral, buccal, sublingual, or by nasal spray. Particular note is made of intrathecal administration. When employing cotreatment with ketamine, doses of from about 10 to about 250 mg are noted.

DETAILED DESCRIPTION OF THE INVENTION

The terms "polypeptide," "peptide" and "protein" are used interchangeably herein to refer to a polymer of amino acid residues. The terms are to be broadly construed also comprising amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, .gamma.-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid such as β-alanine.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

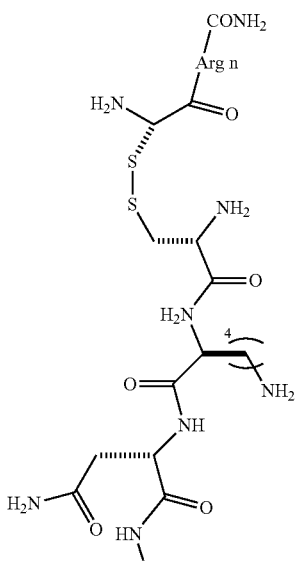

Structure 1

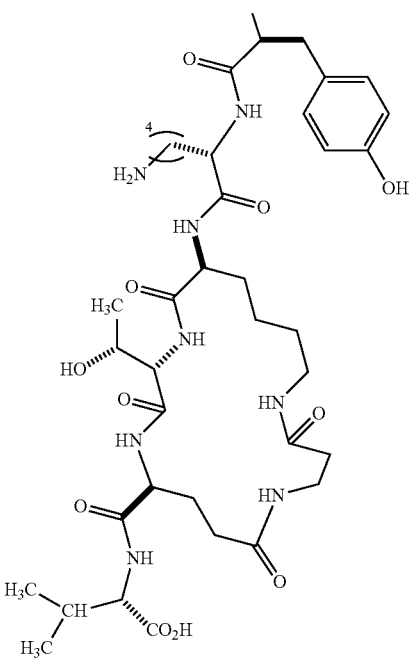

-continued

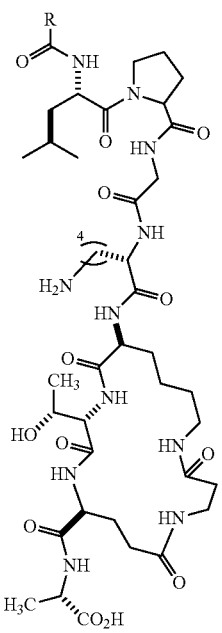

Structure 2

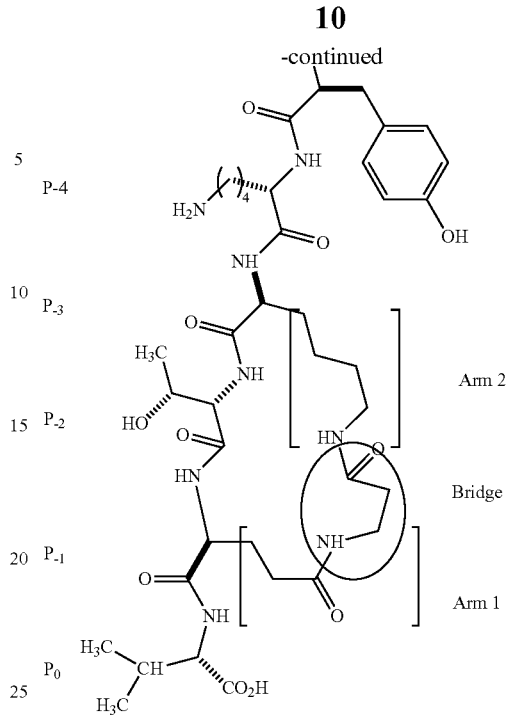

For clarity,

indicates a alkyl chain with a number of carbon atoms, here 4, and a terminal amido group:

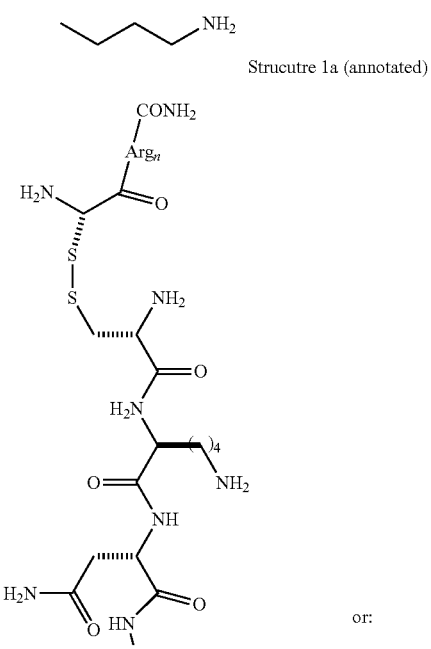

or:

Structures of the present invention can be viewed as linear peptides with a cyclic element. In Structure 1a (an annotated version of Structure 1) the cyclic element is comprised of two amino acid "arms"—Arm 1 and Arm 2, joined by a "bridge" or "variable region" element, here beta-alanine (β-alanine), and amino acid, $P_{-2}$. In this example, Arm 1 is glutamic acid (the amino acid in the $P_{-1}$ position), Arm 2 is lysine (the amino acid in the $P_{-3}$ position), along with the amino acid of $P_{-2}$ and the bridge element. The bridge element is contemplated as comprising from a single amino acid to 6 or more amino acids, though particular note is made of a the bridge element comprising a single amino acid or two or three amino acids. Covalent linkage of the bridge element is particularly contemplated.

These cyclic elements can be formed of any amino acids offering great variability is size and side chain availability. These elements offer increased stability against proteases, enhanced binding selectivity and enhanced ability to modify/select permeability.

Associated with this cyclic moiety is a segment to facilitate cell entry of the drug. This is termed an "Incorporation Sequence." In some embodiments this includes from 1 to 5 additional amino acids as linker elements linking the cyclic element to a transporter element. Molecular transporters included an element known as a poly arginine tail, Structure 3. Incorporation Sequence is broadly defined to cover various molecular transporters that permit insertion into the endosome with or without linker elements. Molecular transporter elements include lipids and liposomes, steroids, polyamines, nanotubes, nanoparticles, dendrimers (including guanidinium terminated dendrimers), cell-penetrating peptides, protein-transduction domains amino acids, peptoids (N-substituted glycines), and oligogcarbamates. Particular note is made of the nuclear transcription activator protein (Tat) which is encoded by HIV type 1. Certain proteins contain subunits that are believed to enable their active translocation across the plasma membrane into cells. In the specific case of HIV-1, this subunit is the basic domain Tat(49-57) (RKKRRQRRR) (SEQ ID NO: 4), the "Tat nonamer." $Arg_7$ below in Structure 3 disclosed as SEQ ID NO: 3.

Structure 3:

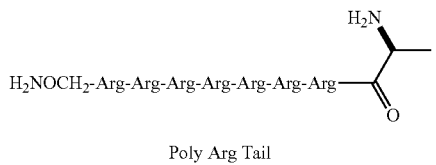

Poly Arg Tail

Also noted as useful molecular transporters are arginine oligomers of about 6-20 units (SEQ ID NO: 2) with particular note of, 7 to 15, and more particularly 8 mer units, D-arginine oligomers, spaced arginine oligomers, and N-arginine peptoids as well as the examples of Table 1. Further noted are oligoarbamate transporters, and tetrameric dendrimers (e.g., Structure 4). Also noted are releasable-luciferin-transporter conjugates.

TABLE 1

Cell-penetrating peptides commonly used for delivery applications

| Cell-penetrating peptide | Amino acid sequence |
|---|---|
| Polyarginines | RRRRRRRRR ($R_9$) (SEQ ID NO: 5) |
| $Tat_{49-57}$ | RKKRRQRRR (SEQ ID NO: 4) |
| Penetratin (Antennapedia) | RQIKIWFQNRRMKWKK (SEQ ID NO: 6) |
| Pep-1 | KETWWETWWTEWSQPKKKRKV (SEQ ID NO: 7) |
| Transportan | GWTLNSAGYLLGKINLKALAALAKKIL (SEQ ID NO: 8) |
| Nuclear localization sequences | VQRKRQKLMP (SEQ ID NO: 9) |
| | SKKKKIKV (SEQ ID NO: 10) |
| | GRKRKKRT (SEQ ID NO: 11) |

Structure 4

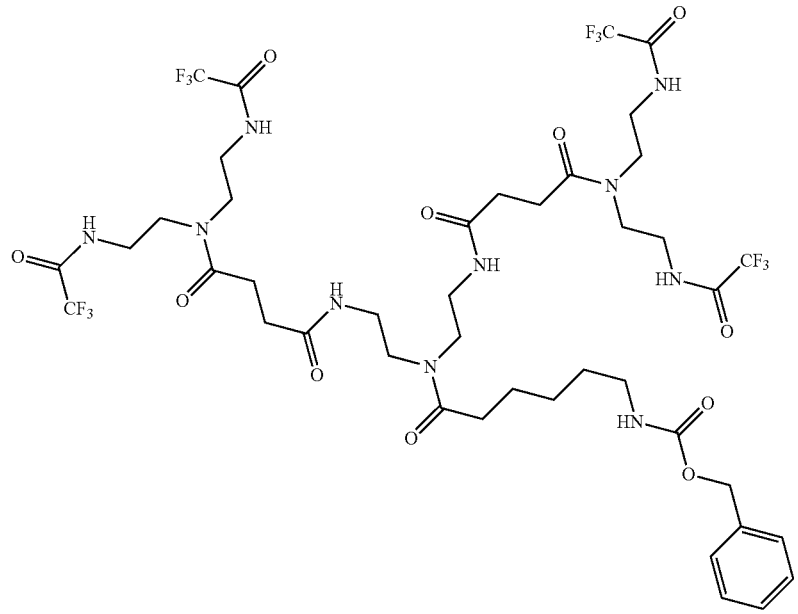

Structure 5
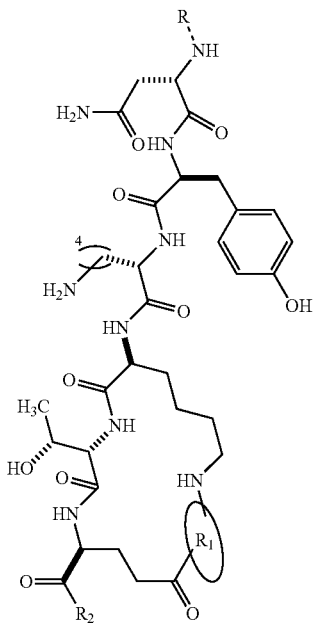

Structure 5 shows reversible inhibitor of at least one neuron-specific PDZ domain which incorporates into the cellular endosome, where R is a molecular transporter (with or without a linker amino acid(s) with particular reference to lysine. $R_1$ is at least about one amino acid covalently bound, and in some embodiments $R_1$ is 2, 3, 4, 5, or 6 amino acids. $R_2$ is isoleucine, leucine, alanine, phenylalanine, and valine. In a specific embodiment, $R_1$ is β-alanine and $R_2$ is valine. In some embodiments the $P_{-4}$ position is usefully occupied by lysine, aspartic acid, glutamic acid and arginine. As shown in Structure 5, the peptide chain extends to $P_{-6}$ position.

Conventional Solid-Phase Synthesis

Synthesis of 1 [(N-Dde)-c[-Lys-Thr-Glu(βAla)-]-Val]

Step I.

Val-NovaSyn TGA resin (n mmol) was loaded into a peptide synthesis reaction vessel. The resin was suspended and swelled (45 min) with shaking using dichloromethane (DCM).

Step II.

Deprotection of the Fmoc group was carried out by adding piperidine-DMF (20% v/v; 10× resin volume) for 10 minutes. Then, piperidine-DMF was drawn off and the resin was treated with fresh piperidine-DMF (20% v/v; 10× resin volume) for another 10 min while shaking. The solvent was drawn off, and the resin was washed with DMF (10× resin volume).

Step III.

Amino acid precursor (3 equiv), DIPCI (4 equiv), HOBt (6 equiv) and DMF (5× resin volume) were mixed within the reaction vessel, and were shaken gently. After 2 h, a small amount of resin sample was removed, placed in a test tube and washed sequentially with DMF (3×1 mL), DCM (3×1 mL) and ether (2×1 mL). The washed sample was submitted to the Kaiser Test. A negative result was indicative of complete coupling.

Step IV.

If the reaction is not complete, additional DIPCI (1 equiv) was added and the vessel shaken for another 2 h. If the coupling was complete, the solution was drawn off and the resin was washed with DMF (10× resin volume).

Steps I-IV.

These protocols were used to synthesize the peptides KTEV (SEQ ID NO: 12) using Dde-Lys(Fmoc)OH and Fmoc-Glu(PhiPr)OH for the $P^{-3}$ and $P^{-1}$ positions, respectively (Scheme 1). The cyclization was accomplished as follows. Using step II, the lysine side chain Fmoc group was removed. Using step III in the linear peptide synthesis protocol, Fmoc-β-alanine (linker) was coupled to the side chain amino group of Lys. The PhiPr protecting group from glutamate was removed using cleavage solution (5× resin volume, TFA/EDT/thioanisole/anisole/DCM (2:4:1:1:92 v/v)) for 30 min. The solution was drawn off and the resin was treated with fresh cleavage solution for another 30 min. This procedure was repeated another two times and finally washed with DMF (10×10× resin volume). A malachite green test was carried out to confirm the presence of free COOH in the resin. Green beads are indicative of free COOH groups. Using step H, the Fmoc group on β-alanine was removed. An aggregation of beads was seen since there is a possibility of forming salt bridges or ionic interactions between the free amino groups and carboxylic acid groups. Then, the resin was washed three times with DIPEA in DMC (10× resin volume, 1:9 v/v; 3 min each time) to wash away any trace piperidine. Finally, the resin was washed with DMF (10× resin volume). This step was followed by the addition of solvent mixture DMSO-N-methylpyrrolidone (NMP) (10× resin volume, 1:4 v/v), which was added to the reaction vessel and gently shaken until the aggregated resin spread out and was evenly suspended in solvent. HBTU (3 equiv), DIEPA (6 equiv), and HOBT (3 equiv) were then added and the vessel shaken gently (Scheme 1).

Scheme 1. Synthetic scheme of compound 1.

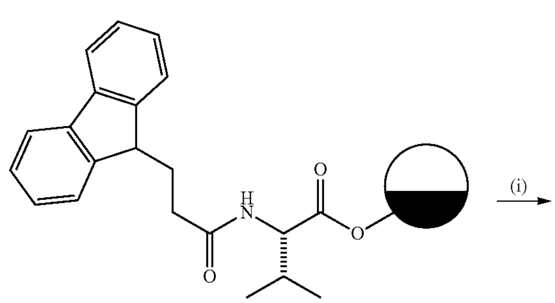

-continued

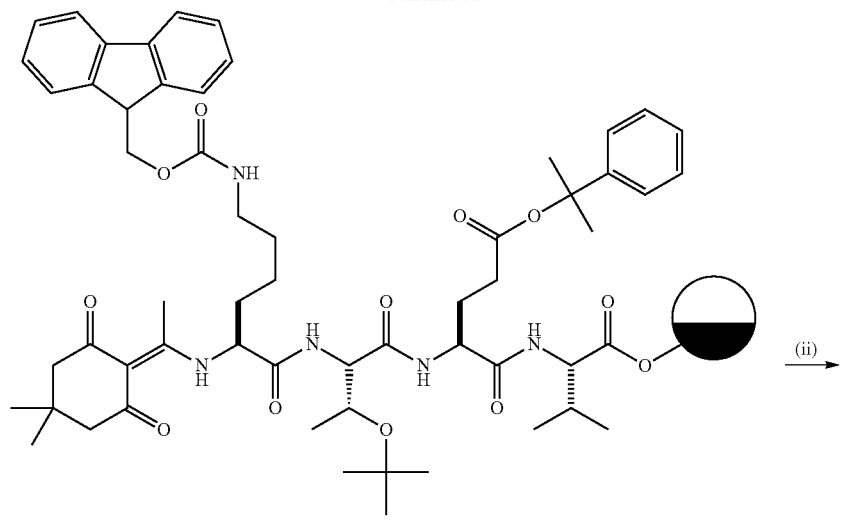

(ii)

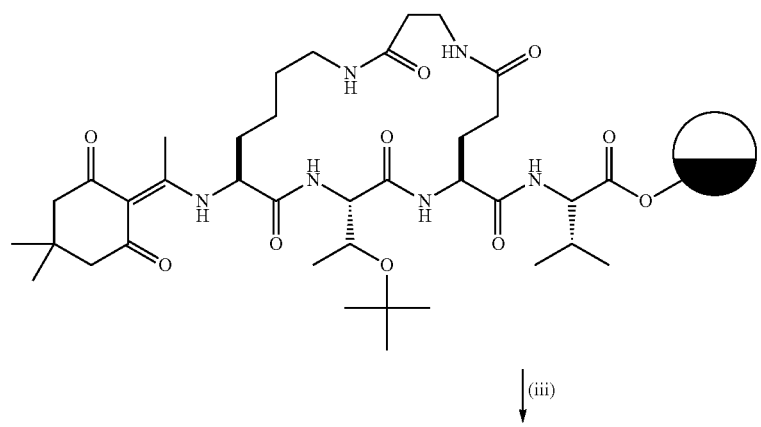

(iii)

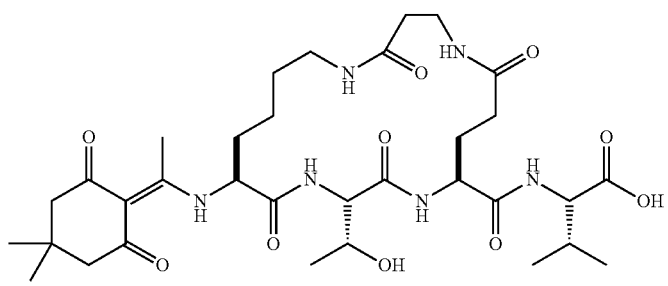

(i) a. 25% piperidine/DMF, b. coupling of Fmoc-Glu(PhiPr)—OH, Fmoc-Thr(OtBu)—OH and Dde-Lys(Fmoc)—OH one at a time using 3 equiv aa, 4 equiv DIPCI, 6 equiv HOBt in DMF with Fmoc-deprotection;
(ii) a. 25% piperidine/DMF, b. 3 equiv Fmoc-βAla-OH, 4 equiv DIPCI, 3 equiv HBTU, 3 equiv HOBt in DMF, c. TFA/EDT/thioanisole/anisole/DCM (2:4:1:1:92 v/v), d. 25% piperidine/DMF, e. 3 equiv HBTU, 6 equiv DIEPA, 3 equiv HOBT in DMSO-NMP (1:4 v/v);
(iii) 2:2:2:94 anisole/thioanisole/triisopropyl silane/TFA, 2 h.

After 2 h, a small amount of resin sample (4-5 mg) was removed and placed in a small test tube, and Kaiser's Test was carried out to check the reaction progress. A negative Kaiser's test was indicative of complete cyclization. If the reaction was complete, the resin was washed with DMF (10×10× resin volume). If the reaction was not complete, the solvent was drawn off and fresh DMSO-N-methylpyrrolidone (NMP) (10× resin volume, 1:4 v/v) was added with HBTU (3 equiv), DIEPA (6 equiv), and HOBT (3 equiv) and the cyclization was repeated (Scheme 2). Whether the reaction was finished or not in the allocated time, the resin was washed with DMF (10×1 mL) in order to avoid epimerization. Finally the resin was washed with DCM (5×10× resin volume). Then, a small amount of resin sample (~20 mg) was removed and resin cleavage solution (5× resin volume, TFA/TIS (triisopropylsilane)/thioanisole/anisole (92:4:2:2, v/v)) was added with shaking for 2 h to obtain compound 1 (Scheme 1). The characterization for compound 1 is shown in Table 2.

first removing the Dde protecting group from the N-terminus lysine (Scheme 2). This deprotection was affected by a deprotection solution (10× resin volume, hydrazine/DMF (3% v/v), 10 min). After 10 min solution was drawn off with a weak vacuum and fresh deprotection solution (10× resin volume, hydrazine/DMF (3% v/v), 10 min) was added while shaking. The Dde group removal procedure was repeated two more times, followed by washing with DMF (10×10× resin volume). The Kaiser's test was performed to confirm Dde removal. A positive result was indicative of the free amino group. Steps II and III were repeated until the desired peptide was synthesized which involved coupling of Fmoc-Lys(Boc)-OH, Fmoc-Tyr(OtBu)-OH, Fmoc-Asp(Trt)-OH, Fmoc-Lys(Boc)-OH and Fmoc-Cys(Trt)-OH. Step II was used to remove the Fmoc group from the N-terminus. Then, a small amount of resin sample (~20 mg) was removed before and

TABLE 2

Compound 1 cyclic peptide synthesis and characterization.

| Peptide No. | Structure | Characterization |
|---|---|---|
| 1 | 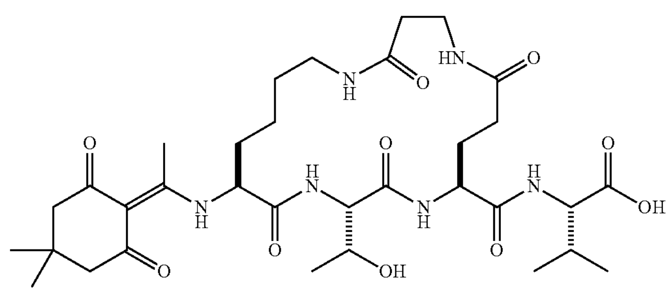 [SMILES: CC(N[C@H]1CCCCNC(=O)CCNC(=O)CC[C@@H](C(=O)N[C@H](C(=O)O)C(C)C)NC(=O)[C@H](C(C)O)NC1=O)=C1C(=O)CC(C)(C)CC1=O] | (N-Dde)-c[-Lys-Thr-Glu(βAla)-]-Val<br>$C_{33}H_{52}N_6O_{10}$<br>Predicted $[M + H]^+$: 694.0<br>ESI-MS found: $[M + H]^+$ 693.0, $[M + Na]^+$ 715.0 |

Synthesis of 3 Cys-Lys-Asn-Tyr-Lys-c[-Lys-Thr-Glu(βAls)-]-Val

When the cyclization was completed as described for the synthesis of 1, the extension of the peptide was carried out by after Fmoc-Cys(Trt)-OH coupling and resin cleavage solution (5× resin volume, TFA/TIS (triisopropylsilane)/thioanisole/anisole (92:4:2:2, v/v)) was added with shaking for 2 h to obtain compound 2 and 3 (Scheme 2). The characterization for compound 2 and 3 are shown in Table 3.

Scheme 2 Synthetic scheme of compound 2.

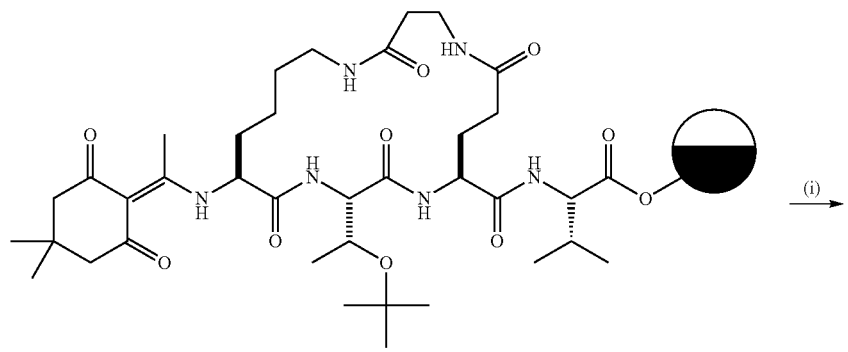

(i)

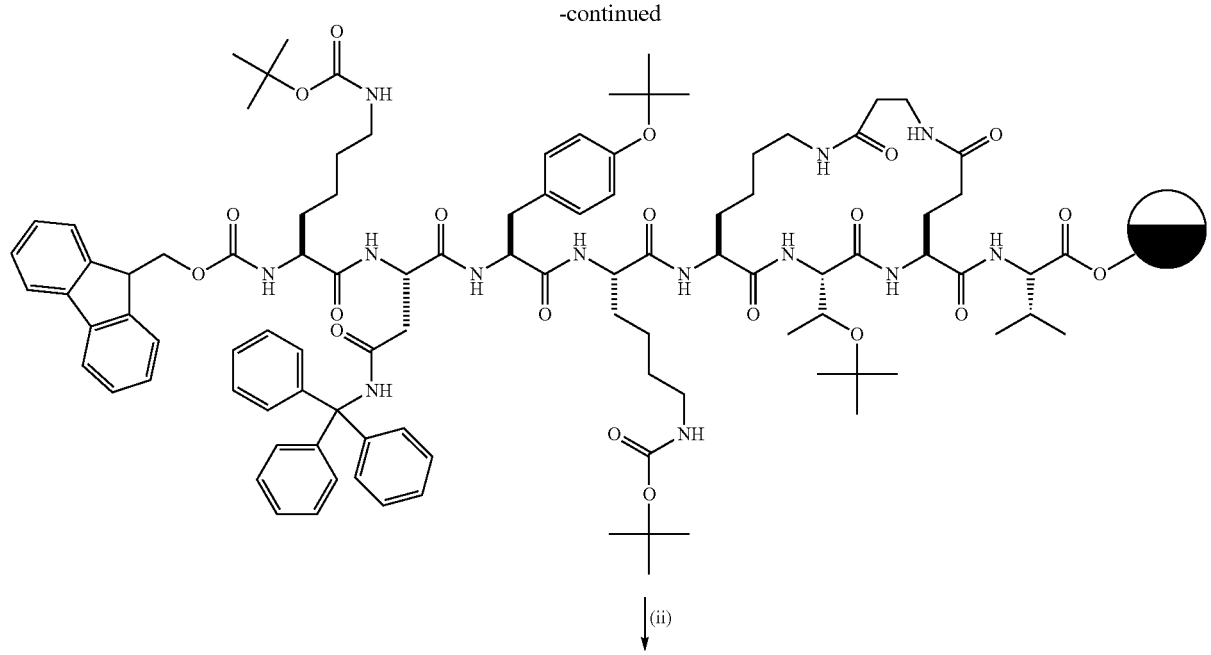

|(ii)

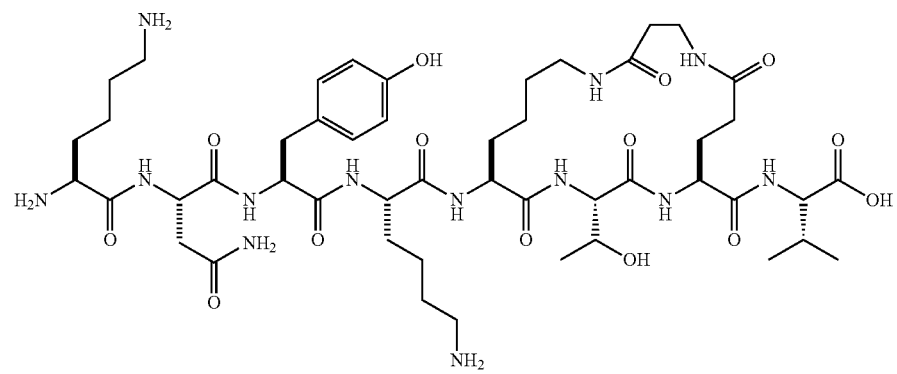

(i) a. 3% hydrazine in DMF, b. coupling of Fmoc-Lys(Boc)—OH, Fmoc-Tyr(OtBu)—OH, Fmoc-Asp(Trt)—OH, and Fmoc-Lys(Boc)—OH one at a time using 3 equiv aa, 4 equiv DIPCI, 6 equiv HOBt in DMF with Fmoc-deprotection;
(ii) a. 25% piperidine/DMF, b. 2:2:2:94 anisole/thioanisole/triisopropylsilane/TFA, 4 h.

The solution was collected and separated equally into two 10 mL test tubes, followed by addition of ethyl ether (−20° C.) to reach 80% of the total tube capacity. The solution was mixed thoroughly and peptide precipitate formed immediately. After centrifugation (8 min, 6000 rpm), the supernatant was decanted, fresh ether was added, and the pelleted peptide was thoroughly mixed before another round of centrifugation (repeated 3 additional times).

TABLE 3

Compounds 2 and 3 cyclic peptide synthesis and characterization.

| Peptide No. | Structure | Characterization |
|---|---|---|
| 2 | [chemical structure] | Lys-Asn-Tyr-Lys-c[-Lys-Thr-Glu(βAla)-]-Val<br>$C_{48}H_{79}N_{13}O_{14}$<br>Predicted [M + H]$^+$: 1063.0<br>MALDI-TOF-MS found: [M + H]$^+$ 1062.6, [M + 2Na]$^+$ 1107.7 |
| 3 | [chemical structure] | Cys-Lys-Asn-Tyr-Lys-c[-Lys-Thr-Glu(βAla)-]-Val<br>$C_{51}H_{84}N_{14}O_{15}S$<br>Predicted [M + H]$^+$: 1166.0<br>MALDI-TOF-MS found:<br>[M + H]$^+$ 1165.4<br>HPLC separation condition: water (in 0.1% TFA): methanol = 80:20 |

Finally, the peptide was dissolved in distilled water (5-10 mL), frozen, and lyophilized for 24-48 h until a white powder was obtained. Peptides were purified by RP-HPLC, and molecular masses confirmed by ESI and MALDI-TOF mass spectroscopy. A small amount of the crude peptide (1 mg) was submitted for mass spectral analysis (ESI-MS and/or MALDI-TOF mass analysis). Each peptide was purified by RP-HPLC (Phenomenex column, 4.6×250 mm, pore size 1 Å). A 3 mg/mL solution of peptide sample was then prepared for analytical scale HPLC. Following the determination of an appropriate solvent system, a peptide sample was prepared (50 mg/mL in water) and submitted to preparative scale HPLC. The peptide-containing fractions were identified and combined, followed by lyophilization. Another analytical scale HPLC was performed after all runs were collected; here all the fractions with peptide were combined and an aliquot of the mixed solution (e.g., 1-5 μL of a 1 mg/mL solution) was injected on to the column under the same conditions to confirm the purity of the isolated peptide. If the fraction showed more than one peak, a repeat of the purification procedure was carried out.

Synthesis of 4 & 5

Synthesis of 4 [(N-Fmoc)-Arg-Arg-Arg-Arg-Arg-Arg-Arg-CONH$_2$] (SEQ ID NO: 3)

The procedure for this peptide was similar to the general linear peptide syntheses, which was manually prepared and purified using standard Fmoc-based solid-phase peptide synthesis protocols. The synthesis of oligoarginine was a particularly difficult synthetic procedure compared to standard linear peptide synthesis. The synthesis was carried out on Rink Amide AM resin (n mmol). The coupling steps were more difficult, and following the coupling of several arginine residues, the beads aggregate after Fmoc-deprotection. The coupling protocol was modified to solve the problem by using pre-activated solutions of arginine.

Coupling of Arginine.

Pre-activation was accomplished by combining DIPEA (4 equiv), HOBT (2.5 equiv), HBTU (2.5 equiv) and DMF (5× resin volume), which were shaken gently for 7 min. Arginine precursor. (3 equiv) was then added. After 2 h, a small amount of resin sample (4-5 mg) was removed and submitted to the Kaiser Test. A negative result was indicative of complete coupling. After the coupling was complete, the reaction solution was drawn off and resin was washed with DMF (10×10× resin volume). Fmoc group removal was effected by the standard procedure, followed by washing with DCM to remove trace DMF (10×10× resin volume). Coupling of arginine was carried out another six times. Small amount of resin beads were cleaved off to confirm the synthesis of compound 4. The cleavage was carried out similar to standard protocols using resin cleavage solution (5× resin volume, TFA/TIS (triisopropylsilane)/anisole (92:6:2, v/v)) after shaking for 28 h. The characterization for compound 4 is shown in Table 4.

TABLE 4

Compound 4 poly-arginine transporter synthesis and characterization.

| Peptide No. | Structure | Characterization |
|---|---|---|
| 4 | 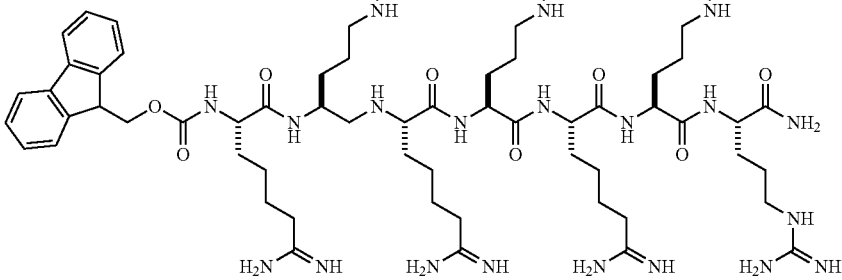 | (N-Fmoc)-Arg-Arg-Arg-Arg-Arg-Arg-Arg-CONH$_2$ (SEQ ID NO: 3) $C_{57}H_{97}N_{29}O_9$ Predicted [M + H]$^+$: 1333.5 MALDI-TOF-MS found: [M + H]$^+$ 1332.8, [M − 156]$^+$ 1176.5, [M − 312]$^+$ 1020.5 |

Synthesis of 5 [Cys(Npys)-Arg-Arg-Arg-Arg-Arg-Arg-Arg-CONH$_2$] (SEQ ID NO: 13)

This procedure was the same as the synthesis of 5, but included an additional coupling of Boc-Cys(Npys)-OH or Fmoc-Cys(Npys)-OH to the N-terminus using general coupling protocols. The characterization for compound 5 is shown in Table 5.

solution slowly developed a bright yellow and the mixture was permitted to stir overnight (14 h) at room temperature. The bright yellow color formation is a confirmation of the Npys (cystine side chain protection) removal in the reaction (FIG. 1). After exhaustive washing steps with DMF, DCM, MeOH, DMSO and ethyl ether (which should remove all the unreacted macrocyclic compound 3), the ligand was cleaved off the beads using cleavage cocktail (5× resin volume, TFA/

TABLE 5

Compound 5 poly-arginine transporter synthesis and characterization.

| Peptide No. | Structure | Characteriazion |
|---|---|---|
| 5 | 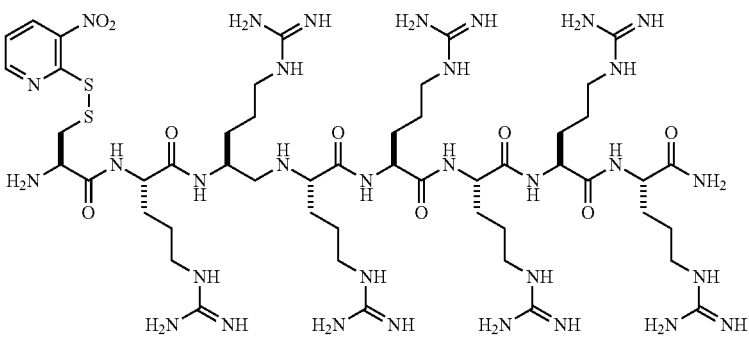 [SMILES: N=C(N)NCCC[C@@H](CN[C@@H](CCCNC(=N)N)C(=O)N[C@@H](CCCNC(=N)N)C(=O)N[C@@H](CCCNC(=N)N)C(=O)N[C@@H](CCCNC(=N)N)C(=O)N[C@@H](CCCNC(=N)N)C(N)=O)NC(=O)[C@H](CCCNC(=N)N)NC(=O)[C@@H](N)CSSc1ncccc1[N+](=O)[O-]] | Cys(Npys)-Arg-Arg-Arg-Arg-Arg-Arg-Arg-CONH$_2$ (SEQ ID NO: 13) $C_{50}H_{94}N_{32}O_{10}S_2$ Predicted [M + H]$^+$: 1367.5, [M + H − (Npys)]$^+$ 1213.5 ESI-MS found: [M + H − (Npys)]$^+$ 1213.5, [M + H − (Npys) − 156]$^+$ 1057.5, [M + H − (Npys) − 312]$^+$ 901.0 |

Synthesis of 6 (Structure 1)

The synthesis was carried out by disulfide coupling of the on-bead oligoarginine compound 5 with previously prepared macrocyclic compound 3 (1.1 equiv). The coupling was performed in 0.1% TFA in DMF (20× resin volume). The orange TIS (triisopropylsilane)/anisole (92:6:2, v/v)) with shaking for 6 h. The lyophilized product of the final product was crystalline, which was a completely different than the white power that was obtained for macrocyclic compound 3. The characterization for compound 6 is shown in Table 6.

TABLE 6

Structure 1 characterization.

| Peptide No. and Code | Structure and Characterization |
|---|---|
| 6 | 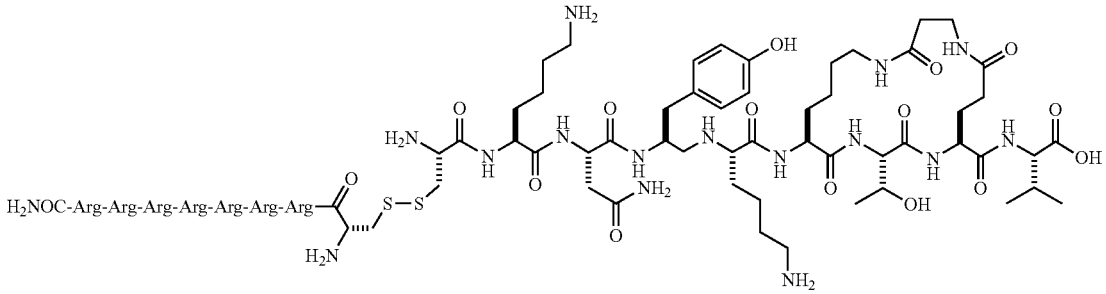 |

Arg₇ above disclosed as SEQ ID NO: 3
CONH₂-(Arg)₇-Cys-Cys-Lys-Asn-Tyr-Lys-c[-Lys-Thr-Glu(βAla)-]-Val
$C_{96}H_{174}N_{44}O_{23}S_2$
Predicted $[M + H]^+$: 2378.0
MALDI-TOF-MS found: $[M + H]^+$ 2384.5, $[M + H - 156]^+$ 22290.0, $[M + H - 312]^+$ 2073.0, $[M - cyclic]^+$ 1213.4, $[M - (C—R_7)Na]^+$ 1164.4
$[M - cyclic + Na - H]^+$ 1235.5
HPLC separation condition: water (in 0.1% TFA): methanol = 75:25

Synthetic Protocol for Structure 1

Microwave Solid-Phase Synthesis

Structure 1 was synthesized on Rink amide AM (0.6 mmol/g, Novabiochem) resin (cat no. 01-64-0038) using microwave solid phase peptide synthesis protocols developed in our lab. The synthesis was carried out by disulfide coupling of the on-bead oligoarginine compound 5 with previously prepared macrocyclic compound 3 (~1.1 equiv).

Synthesis of 3 Cys-Lys-Asn-Tyr-Lys-c[Lys-Thr-Glu(βAla)-]-Val

The macrocyclic compound 3 was synthesized on Fmoc-Val NovaSyn TGA resin (N mmol, 0.2 mmol/g, cat. no. 04-12-2671). After the initial Fmoc deprotection using 25% piperidine in DMF MW, 70° C., 6.5 min, coupling of Fmoc-Glu(PhiPr)-OH was carried out using 5 equiv Fmoc-Glu(PhiPr)-OH, 5 equiv HBTU in DMF, MW, 70° C., 8 min followed by Fmoc deprotection using 25% piperidine in DMF MW, 70° C., 6.5 min as previously described. Then Fmoc-Thr(OtBu)-OH and Dde-Lys(Fmoc)-OH one after another using 5 equiv Fmoc-as-OH, 5 equiv HBTU in DMF, MW, 70° C., 8 min for amino acid coupling and 25% piperidine in DMF MW, 70° C., 6.5 min, for Fmoc deprotection. After the Fmoc deprotection of lysine side chain, Fmoc-βAla-OH was coupled using 5 equiv Fmoc-βAla-OH, 5 equiv HBTU in DMF, MW, 70° C., 8 min. This step was followed by PhiPr group deprotection of glutamate side-chain using 2% TFA, 2% triisopropyl silane, 2% triethylsilane in 1,2 dichloromethane, 70° C., 15 min. following PhiPr group deprotection, the N-terminal βAla Fmoc group was deprotected using 25% piperidine in DMF MW, 70° C., 6.5 min. Then on-bead cyclization followed using 3 equiv HBTU, 3 equiv HCTU, DMF, MW, 70° C., 12 min. After the cyclization the extension of the peptide was carried out by first removing the Dde protecting group from the N-terminus lysine. The Dde group was deprotected using 5% hydrazine monohydrate in DMF MW, 70° C., 7.5 min. This step was followed by coupling of Fmoc-Lys(Boc)-OH, Fmoc-Tyr(OtBu)-OH, Fmoc-Asp(Trt)-OH, Fmoc-Lys(Boc)-OH and Fmoc-Cys(Trt)-OH using 5 equiv Fmoc-aa-OH, 5 equiv HBTU in DMF, MW, 70° C., 8 min for coupling step followed by Fmoc deprotection using 25% piperidine in DMF MW, 70° C., 6.5 min. Then the beads were thoroughly washed with DMF, DCM, ethyl ether. Finally the side chain deprotection and resin cleavage was effected by treating with 2% anisole, 2% thioanisole, 2% triisopropyl silane, 94% TFA, MW, 40° C. for 30 min. Compound 3 was purified by RP-HPLC, and molecular masses confirmed by MALDI-TOF mass spectroscopy.

Synthesis of 5 [Cys(Npys)-Arg-Arg-Arg-Arg-Arg-Arg-Arg-CONH₂] (SEQ ID NO: 13)

The compound 5 was synthesized on Rink amide AM (0.6 mmol/g, Novabiochem) resin (cat no. 01-64-0038) using microwave solid phase peptide synthesis protocols. The initial Fmoc deprotection using 25% piperidine in DMF MW, 70° C., 6.5 min, was followed by coupling of Fmoc-Arg(Pbf)-OH was carried out using 5 equiv Fmoc-Arg(Pbf)-OH, 5 equiv HBTU in DMF, MW, 70° C., 10 min followed by Fmoc deprotection using 25% piperidine in DMF MW, 70° C., 6.5 min. The coupling of Fmoc-Arg(Pbf)-OH was repeated another six times to give the Fmoc-Arg(Pbf)-(Arg(Pbf))-6-on-bead (SEQ ID NO: 14). This was followed by the N-terminal Fmoc deprotection of Arginine followed by coupling of Boc-Cys(Npys)-OH using 5 equiv Boc-Cys(Npys)-OH, 5 equiv HBTU in DMF, MW, 60° C., 8 min. The synthesis of compound 5 was carried out prior to the final on-bead disulfide coupling to give compound 6 (Structure 1).

Synthesis of Compound 6 (Structure 1)

The synthesis was carried out by disulfide coupling of the on-bead oligoarginine compound 5 with previously prepared macrocyclic compound 3 (~1.1 equiv). Boc-Cys(Npys)-(Arg (Pbf))$_7$-on-bead (SEQ ID NO: 15) (N mmol) resin was first thoroughly washed with DMF, DCM, methanol, ethyl ether. Then a solution was prepared using ~N mmol of compound 3 in 0.1% TFA in DMF and added to Boc-Cys(Npys)-(Arg (Pbf))$_7$-on-bead (SEQ ID NO: 15). Then the mixture was reacted for 12 min, MW, 70° C. The mixture was allowed to come to room temperature while shaking and allowed to shake for another 1 hr. The orange solution developed a bright yellow mixture at this stage indicative of the Npys (cystine side chain protection) removal in the reaction. After exhaustive washing steps with DMF, DCM, MeOH, DMSO and ethyl ether, the ligand was cleaved off the beads using cleavage cocktail 2% anisole, 2% thioanisole, 2% triisopropyl silane, 94% TFA, MW, 40° C. for 45 min. Compound 6 was purified by RP-HPLC, and molecular masses confirmed by MALDI-TOF mass spectroscopy.

One aspect of the present invention usefully employs electrophysiological screening of Structure 1. Particular attention is drawn to an electrophysiological assay that rapidly screens for compounds which are inhibitors that target neuron-specific PDZ domains. Recordings of cellular activity were made from acute slices of rat retinal and brain tissue to examine the effects of Structure 1 on synaptic Kainate/AMPA, NMDARs and to test for protection against excitotoxic insults. Kainate/AMPA and NMDAR components were distinguished pharmacologically. Noted are the selective AMPA-antagonist NBQX and the competitive NMDA-antagonist CPP. A multielectrode array was used that enabled examination of activity from sixty neurons simultaneously. This array addressed whether a test compound provided neuroprotection against kainate or N-methyl-D-aspartic acid (NMDA)-induced death. Briefly, slices were perfused for prolonged periods (about 30 min) with NMDA or kainate agonists until activity in half of the neurons is lost and responses cannot be rescued by washing out the NMDA or kainate (assumed to be resulting from neuronal death). Pretreatment with the compound of Structure 1 (30 uM) or cotreatment with the compound of Structure 1 and an NMDA receptor agonist provided efficacy and potency in preventing neuronal death. In a test, this dose of 30 uMolar prevented cell death.

In addition to the retinal tissue as a model for Stroke, compounds of the present invention were tested in hippocampal neurons by delivering an excitotoxic insult, commensurate with a Stroke, which resulted in the permanent loss of functional activity in these cells. This loss was prevented by the co-application of the compound of Structure 1. Results were confirmatory of the retinal data and extends it into tissues that are more strongly associated with CNS disorders such as Stroke and neurodegenerative diseases. Noted is therapeutic treatment for autism disorders and cognitive decline symptomatology conditions.

The compounds of the present invention were further tested on synaptic plasticity and in particular LTP (long-term potentiation) in the hippocampus. Data indicated enhanced induction and magnitude of LTP. It is noted that LTP is widely considered to be the basis for learning and memory and enhancements and deficits in LTP have been reported as correlated with increased and decreased performance in behavioral tests that measure these phenomena, respectively.

Attention is drawn to pretreatment by administration of a therapeutically effective amount of a composition of Structure 5 about 48 to about ½ hour in advance of neuro-stress, and particularly about within 6 hrs of the neuro-stress event. For post neuro-stress treatment administration as soon as possible is noted. Administration within 30 minutes to one hour from onset of neuro-stress is particularly noted. Noted are single doses from about 0.1 uM to about 100 uM, or continuous infusions of 0.01-5 μM/hr via intrathecal; intraventrical or intravitral routes.

Investigation further included monitoring the selective uptake of the poly-arginine (Structure 3)—and the mysterolated-tailed PDZ-mimic (e.g., Structure 1 and 2) tagged with a fluorescent marker crossed the vitreal/retina barrier when administered intravitrealy and was shown to readily cross the pia mater/brain barrier and localize in neurons deep to these barriers within the retina, spinal cord and brain.

Uptake in the retina was observed as follows. Retinas exposed to 1.5-6 nmol of Structure 1 compound showed about a 50% uptake pattern, 6 hrs-following intravitreal injection. In numerous populations of retinal neurons located in both the ganglion cell (GCL) and inner nuclear layers. Structure 1 compound also selectively accumulated within ganglion cell axons as evident by their intense labeling at the optic nerve head. These results provide evidence that an intravitreal injection of Structure 1 reaches neurons that are sensitive to glutamate excitotoxicity within the retina and axonal fibers that are unsheathed by mylenated covering within the optic nerve, which are also known sites sensitive to glutamate excitotoxicty.

Example 1

Intrathecal Injection

Intrathecal injection of Structure 1 compound in rats was tested. Rats were prepped for intrathecal injection containing 16 nmol of Structure 1 compound at the level of CV2. 24 hrs following the injection the rats were perfused with 4% PFA and frozen cross-sections of the cord were mounted on glass slides and photographed. Structure 1 composition crosses the pia mater/brain barrier and selectively accumulates in neurons located within the gray matter of the cord. Uptake of Structure 1 compound occurred in the cord at the site of the injection (high cervical region of the cord), and was shown to label neurons within the gray area from high cervical, all the way down to the conus medularis. In addition, the labeled peptide was also shown to accumulate in cells located in the cortex, hippocampus, brainstem and striatum with these cervical injections. These data indicate that intrathecal delivery of Structure 1 is useful to preload all spinal cord neurons with the PDZ-mimic and provide neuroprotection.

The compound of this invention are useful in the therapeutic treatment of neurological insult such as stroke, traumatic brain injury, epilepsy as well as for pain and neurodegenerative disease (collectively, "neuro-stress"). Particular note is made of the prophylactic treatment of neuro-stress by administering a therapeutic dosage in advance of insult. This method is available, for example, prior to a surgical procedure that would invade the brain. Without being bound by any particular theory it is believed stroke and other neurological insults entail brain cells being starved of oxygen, glucose, nutrients and an associated build up of waste materials, that include glutamate, leading to an excitotoxic insult. The neurons of the stroke patient become hyper-excitable due to the release of large concentrations of glutamate (10-fold greater than basal) which activate receptors including extrasynaptic NMDA receptors). This leads to the gating of large amounts of calcium though these normally quiet receptors. The intracellular calcium concentration rises from basal levels (0.05-0.2 uM) to a level (1 uM) that triggers the activation of cell death pathways and the result is brain damage to the affected areas of the brain. Compounds of the present invention are usefully administered at therapeutic doses within about 30 minutes to 1 hour. In some instances an oral formulation, a nasal spray or an acute injection given i.v. or intrathecally to induce a therapeutic concentration in the brain is indicated. This protects neural tissue. Particular note is made of drug administration which, at therapeutic levels, interferes with the signal mediated by the rising levels of calcium so that the elevated calcium does not trigger the cell death pathway. As the ischemic condition abates and calcium levels return to normal the patient recovers and brain damage has been averted.

Example 2

Therapeutic Protocol in Stroke

A 48 year old female presents with an ischemic episode resulting sudden numbness the face, and left arm, confusion, and trouble speaking. Within 2 hours of onset, Structure 1 composition is administered at 50 mg/Kg i.v. Within 48 hours the patient recovers without significant brain damage. Doses of from about 1 to about 100 mg/Kg are noted.

The compositions of this invention possess valuable pharmacological properties. They are useful in the treatment of stroke or anoxic brain injury. This effect can be demonstrated, for example, using the method of prompt administration upon neurological insult. Administration is contemplated to include chronic, acute or intermittent regimens.

The pharmacologically active compositions of this invention can be processed in accordance with conventional methods of Galenic pharmacy to produce medicinal agents for administration to patients, e.g., mammals including humans.

The compositions of this invention can be employed in admixture with conventional excipients, i.e., pharmaceutically acceptable organic or inorganic carrier substances suitable for parenteral, or enteral (e.g., oral or inhalation) use which do not deleteriously react with the active compositions. Suitable pharmaceutically acceptable carriers include but are not limited to water, salt solutions, e.g., saline. The pharmaceutical preparations can be sterilized and if desired mixed with auxiliary agents, e.g., 1 salts for influencing osmotic pressure, buffers and the like which do not deleteriously react with the active compositions. They can also be combined where desired with other active agents, e.g., TPA (Tissue Plasminogen activator).

In some embodiments of the present invention, dosage forms include instructions for the use of such compositions.

For parenteral application, particularly suitable are injectable, sterile solutions, preferably oily or aqueous solutions, as well as suspensions, emulsions, or implants, including suppositories. Ampules are convenient unit dosages.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

Generally, the compositions of this invention are dispensed in unit dosage form comprising about 1 to about 100 mg in a pharmaceutically acceptable carrier per unit dosage.

The dosage of the compositions according to this invention generally are 1 to 100 mg/kg/day, preferably 1 to 10 (especially if the general dosage range spans an order of magnitude or more), when administered to patients, e.g., humans to treat (e.g., cardiac insufficiency) analogously to the known agent (hydrochlorothiazide (HydroDIURIL®), and is to 25-50 mg daily TID mg/kg/day when administered to treat (hypertension); (repeat for all activities and indications). Alternatively, treat as an IV bolus, then IV infusion similar to Thrombolytic agents such as alteplase (TPA), or antiarrhythmic drugs e.g. atenolol (IV 50 10 mg) or anti-Parkinson drugs benztropine (Congentin®) IV 1-6 mg daily, or entacapone 200-1,600 mg.

It will be appreciated that the actual preferred amounts of active compositions in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol.

The invention claimed is:

1. A composition which is reversible inhibitor of at least one neuron-specific PDZ domain comprising:

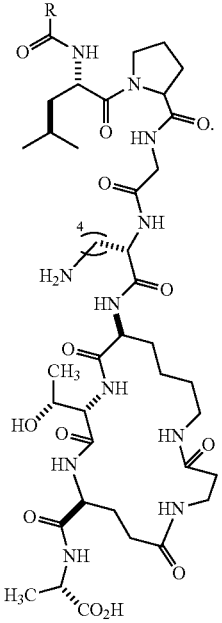

Structure 2 where n is about 6 to 20 units.

2. A method of treatment of neuro-stress comprising administering to a subject a therapeutically effective amount of the composition of claim 1.

3. The method of claim 2 wherein the neuro-stress is stroke.

4. The method of claim 2 wherein said administration is in advance of said neuro-stress.

5. The method of claim 2 further compromising cotreatment with a therapeutically effective amount of an NMDA receptor agonist.

6. The method of claim 5 wherein said NMDA receptor agonist is selected from the group comprising AMPA, kainate, ketamine and NMDA.

7. The method of claim 2 wherein said therapeutic effective dose of the composition of claim 1 is from about 0.1 μM to about 100 μM.

8. The method of claim 7 wherein said dosage is from about 20 μM to about 40 μM.

9. The method of claim 2 wherein administration is parenteral, oral, buccal, sublingual, or by nasal spray.

10. The method of claim 9 wherein administration is intrathecal.

11. The method of claim 6 wherein said receptor agonist is ketamine from about 10 to about 250 mg.

12. A composition which is reversible inhibitor of at least one neuron-specific PDZ domain comprising:

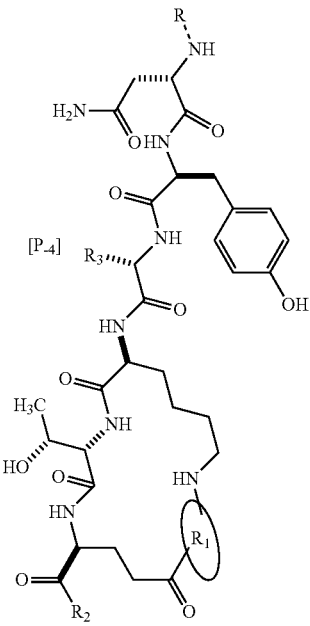

Structure 5 wherein
R is a molecular transporter including 7 contiguous arginines with or without a linker amino acid;
$R_1$ is at least about one amino acid covalently bound; and,
$R_2$ is isoleucine, leucine, alanine, phenylalanine, or valine and having a $P_{-4}$ position, and,
$R_3$ is one side chain moiety selected from the group consisting of lysine, arginine, glutamic acid or aspartic acid.

13. A method of treatment of neuro-stress comprising administering to a subject a therapeutically effective amount of the composition of claim 12.

14. The method of claim 13 wherein the neuro-stress is selected from the group comprising stroke, traumatic brain injury, epilepsy, pain or neurodegenerative disease.

15. The method of claim 13 wherein said administration is in advance of said neuro-stress.

16. The method of claim 13 further compromising cotreatment with a therapeutically effective amount of an NMDA receptor agonist.

17. The method of claim 16 wherein said NMDA receptor agonist is selected from the group comprising AMPA, kainate, ketamine and NMDA.

18. The method of claim 13 wherein said therapeutic effective dose of the composition of claim 12 is from about 0.1 μM to about 100 μM.

19. The method of claim 18 wherein said dosage is from about 20 μM to about 40 μM.

20. The method of claim 13 wherein administration is parenteral, oral, buccal, sublingual, or by nasal spray.

21. The method of claim 20 wherein administration is intrathecal.

22. The method of claim 17 wherein said receptor agonist is ketamine from about 10 to about 250 mg.

* * * * *